(12) United States Patent
Morris (10) Patent No.: US 6,544,199 B1
(45) Date of Patent: Apr. 8, 2003

(54) SYSTEMS AND METHODS FOR MODIFYING BEHAVIORAL DISORDERS

(76) Inventor: Donald E. Morris, 44 Marguerita Rd., Kensington, CA (US) 94707

(*) Notice: Subject to any disclaimer, the term of this patent is extended or adjusted under 35 U.S.C. 154(b) by 0 days.

(21) Appl. No.: 09/517,142

(22) Filed: Mar. 2, 2000

Related U.S. Application Data (62) Division of application No. 09/079,207, filed on May 14, 1998, now Pat. No. 6,093,158.
(60) Provisional application No. 60/046,622, filed on May 15, 1997.

(51) Int. Cl.[7] .................................................. A61B 5/00
(52) U.S. Cl. ...................................................... 600/590
(58) Field of Search ............................. 600/546, 559, 600/587, 590

(56) References Cited

U.S. PATENT DOCUMENTS

| | | |
|---|---|---|
| 2,999,232 A | 9/1961 | Wilson |
| 3,480,010 A | 11/1969 | Crossley |
| 4,129,125 A | 12/1978 | Lester et al. |
| 4,220,142 A | 9/1980 | Rosen et al. |
| 4,390,028 A | 6/1983 | Okano et al. |
| 4,402,326 A | 9/1983 | Okano et al. |
| 4,521,186 A | 6/1985 | Wodlinger et al. |
| 4,593,686 A | 6/1986 | Lloyd et al. |
| 4,617,525 A | 10/1986 | Lloyd |
| 4,629,424 A | 12/1986 | Lauks et al. |
| 4,669,477 A | 6/1987 | Ober |
| 4,715,367 A | 12/1987 | Crossley |
| 4,802,485 A | 2/1989 | Bowers et al. |
| 4,830,008 A | 5/1989 | Meer |
| 4,838,283 A | 6/1989 | Lee, Jr. |
| 4,842,519 A | 6/1989 | Dworkin |
| 4,934,378 A | 6/1990 | Perry, Jr. |
| 4,944,310 A | 7/1990 | Sullivan |
| 4,976,618 A | 12/1990 | Anderson |
| 4,979,516 A | 12/1990 | Abraham, II |
| 4,982,738 A | 1/1991 | Griebel |
| 4,989,616 A | 2/1991 | Lee |
| 4,995,404 A | 2/1991 | Nemir |
| 5,036,865 A | 8/1991 | Keaton |
| 5,038,137 A | 8/1991 | Lloyd |
| 5,078,153 A | 1/1992 | Nordlander et al. |
| 5,081,447 A | 1/1992 | Echols |
| 5,123,425 A | 6/1992 | Shannon, Jr. et al. |
| 5,133,354 A | 7/1992 | Kallok |
| 5,146,918 A | 9/1992 | Kallok et al. |
| 5,174,287 A | 12/1992 | Kallok et al. |
| 5,178,156 A | 1/1993 | Takishima et al. |
| 5,190,048 A | 3/1993 | Wilkinson |
| 5,190,051 A | 3/1993 | Wilson |
| 5,203,343 A | 4/1993 | Axe et al. |
| 5,211,173 A | 5/1993 | Kallok et al. |
| 5,215,082 A | 6/1993 | Kallok et al. |

(List continued on next page.)

Primary Examiner—Max F. Hindenburg
(74) Attorney, Agent, or Firm—Bingham McCutchen, LLP; David G. Beck (57) ABSTRACT

A system is provided for monitoring an undesired behavioral disorder such as bruxism, jaw clenching, or snoring. A processor correlates the monitored behavior with the onset of the undesired disorder. Since behavior of this type is typically subconscious, the sensor is preferably coupled to a warning device to alert the patient when he or she is performing the undesired behavior. Typically the warning device causes the patient to experience an unpleasant sensation, thus promoting the discontinuance of the behavior. In one embodiment the system determines which stimuli is most effective and therefore best suited for an individual patient. The system may further include means to record the monitored data related to the undesired behavioral disorders. This feature allows the patient to receive data related to the rate, duration, intensity, and time of day that the unconscious behavior occurred thus allowing the patient to correlate the undesired behavior with outside factors.

18 Claims, 6 Drawing Sheets

U.S. PATENT DOCUMENTS

| | | |
|---|---|---|
| 5,238,006 A | 8/1993 | Markowitz |
| 5,251,636 A | 10/1993 | Neuman |
| 5,265,624 A | 11/1993 | Bowman |
| 5,277,193 A | 1/1994 | Takishima et al. |
| 5,284,161 A | 2/1994 | Karell |
| 5,295,490 A | 3/1994 | Dodakian |
| 5,300,094 A | 4/1994 | Kallok et al. |
| 5,301,689 A | 4/1994 | Wennerholm |
| 5,311,875 A | 5/1994 | Stasz |
| 5,335,657 A | 8/1994 | Terry, Jr. et al. |
| 5,357,981 A | 10/1994 | Eilam et al. |
| 5,381,801 A | 1/1995 | McShane et al. |
| 5,383,475 A | 1/1995 | Austin |
| 5,394,883 A | 3/1995 | Neuman |
| 5,413,111 A | 5/1995 | Wilkinson |
| 5,458,105 A | 10/1995 | Taylor et al. |
| 5,477,860 A | 12/1995 | Essen-Moller |
| 5,477,867 A | 12/1995 | Balkanyi |
| 5,483,969 A | 1/1996 | Testerman et al. |
| 5,485,851 A | 1/1996 | Erickson |
| 5,490,520 A | 2/1996 | Schaefer et al. |
| 5,522,862 A | 6/1996 | Testerman et al. |
| 5,537,997 A | 7/1996 | Mechlenburg et al. |
| 5,540,731 A | 7/1996 | Testerman |
| 5,540,732 A | 7/1996 | Testerman |
| 5,540,733 A | 7/1996 | Testerman et al. |
| 5,546,952 A | 8/1996 | Erickson |
| 5,549,655 A | 8/1996 | Erickson |
| 5,553,626 A | 9/1996 | Burger et al. |
| 5,558,099 A | 9/1996 | Bowman et al. |
| 5,573,004 A | 11/1996 | Groenke |
| 5,586,562 A | 12/1996 | Matz |
| 5,588,439 A | 12/1996 | Hollub |
| 5,591,216 A | 1/1997 | Testerman et al. |
| 5,671,733 A | 9/1997 | Raviv et al. |
| 5,792,067 A | 8/1998 | Karell |

SYSTEMS AND METHODS FOR MODIFYING BEHAVIORAL DISORDERS

This is a Division of application Ser. No. 09/098,207 filed May 14, 1998 now U.S. Pat. No. 6,093,158, and claims the benefit of provisional application No. 60/046,622, filed May 15, 1997.

BACKGROUND OF THE INVENTION

The present invention relates to a system and method for the treatment of sleeping disorders such as bruxism, jaw clenching, and snoring. Bruxism is the abnormal excessive and non-functional nocturnal or subconscious grinding of teeth which may or may not be associated with jaw clenching. Snoring is typically related to the manner of breathing (i.e., through the mouth as opposed to through the nose), the sleeping position (i.e., on the back versus on the side), or both.

At a minimum, bruxism and jaw clenching will typically result in excessive tooth wear and periodontal problems. Unfortunately in many cases this clenching or bruxing action not only damages the teeth themselves, but also the supporting structure of the teeth including both the hard bony material and the soft tissue. As a result, in more extreme cases these disorders lead to TMJ, jaw displacement, stiff neck, and severe headaches. Research on bruxism has shown that bruxism is linked with stress. Although not everyone who bruxes is under stress, it has been shown that some people grind their teeth more after a tense day, or in the anticipation of stress. As stress, or the perception of stress occurs, bruxism is likely to occur.

Snoring, unlike bruxism, may or may not be related to stress. Typically snoring is simply a consequence of how a person breathes while they sleep or the position in which they sleep. Often snoring is symptomatic of another problem, such as an allergy, which affects the way in which a person breathes. Therefore once a solution is found to the root problem, the snoring problem may disappear. Unfortunately not all snoring is related to such a solvable root problem.

One traditional treatment for teeth grinding involves placing a protective layer of acrylic material, generally referred to as a splint, over the involved teeth. This acrylic layer serves to protect the teeth from direct contact, thus reducing wear, and to spread the load caused by clenching so that it is shared more equally among the neighboring teeth. This reduces wear of the teeth, but the acrylic protective layer does not address the problem of clenching, which frequently continues indefinitely. In some cases the urge to clench is worsened.

A second traditional treatment for clenching is occlusal adjustment. This treatment involves selective grinding of teeth so that the load on the teeth caused by clenching is carried evenly by several teeth rather than being concentrated on one or two. This technique is successful with some but not all types of clenching. However, if not carefully practiced, it can lead to subsequent legal liability which is enhanced because of the permanent nature of the procedure.

Since bruxism is generally the result of stress, typical traditional solutions which focus on guarding against the physical consequences of bruxing fail to permanently relieve the patient. A permanent solution must lie either in eliminating the stress causing agent or in improving stress management skills.

One method of treating both bruxism and snoring is behavior modification. Behavior modification typically involves directing a stimulus, sometimes an unpleasant one, at the patient whenever he or she practices the undesirable behavior. Thus the patient gradually learns not to perform the undesirable behavior, thus avoiding the unpleasant stimulus.

U.S. Pat. No. 4,934,378 discloses a system for monitoring bruxism by measuring the electrical signals emitted by the jaw muscles. The monitoring apparatus is mounted on a probe that is inserted into one of the user's ear channels. When the system detects jaw muscle activity associated with bruxism, it alerts the user, for example by emitting an audible tone or a prerecorded message.

U.S. Pat. No. 4,715,367 discloses a behavioral modification device which may be used to detect and treat snoring, bruxism, and sleep apnea. The patent discloses the use of pressure sensors mounted on either side of the forehead and actuated by flexing the temporal muscles. The patent also discloses using microphones to sense breathing and snoring. The output of the system is a regulatable electric shock applied to the user through a neck collar.

U.S. Pat. No. 5,477,867 discloses a device for use in suppressing snoring. A microphone, either a throat microphone or a microphone mounted in a headband, detects the snoring noises. Once detected, a sound generator capable of generating a plurality of tones of varying intensity is used to transmit a sound to the user in order to modify their behavior. The tone and intensity composition of the sound may either be varied randomly or in response to the detected snoring.

Although a variety of different systems have been devised to prevent and/or modify a person's tendency towards snoring, bruxism, and jaw clenching, these systems have typically met only limited success for a variety of reasons. For example, many systems are unreasonably uncomfortable, making normal sleep or day time use impossible. Therefore an improved method of modifying a person's behavior, specifically behavior associated with bruxism, jaw clenching, or snoring, is desirable.

SUMMARY OF THE INVENTION

The present invention provides at least one technique for monitoring an undesired behavioral disorder such as bruxism, jaw clenching, or snoring. A processor correlates the monitored behavior with the onset of the undesired disorder. Since behavior of this type is typically subconscious, the sensor is preferably coupled to a warning device to alert the patient when he or she is performing the undesired behavior. Typically the warning device causes the patient to experience an unpleasant sensation, thus promoting the discontinuance of the behavior. In one aspect of the invention, the system determines which stimulus is most effective and therefore best suited for an individual patient. The invention may also include means to record the monitored data related to the undesired behavioral disorders. This feature allows the patient to receive data related to the rate, duration, intensity, and time of day that the unconscious behavior occurred thus enabling the patient to correlate the behavior with outside factors (e.g., stress, lack of sleep, etc.).

A variety of different sensor types may be used with the present invention. For example, the sensor may monitor sounds (e.g., snoring, teeth grinding) emitted by the patient during the undesirable behavior. These sounds may be monitored with a microphone that detects the audible sounds, or with a microphone that detects sounds that are conducted by the patient's body tissues. Alternatively, the sensor may monitor changes in a group of muscles that are effected by the behavioral disorder. For example, muscles within the jaw and the temple contract during jaw clenching. Changes in a muscle group may be determined by monitoring such muscle properties as density, resiliency, electrical conductivity, electrical activity, elasticity, and thickness.

The stimulus from the system's warning device may take any form, alone or in combination, that causes the patient to alter their behavior. For example, the device may produce an odor, a change in temperature, an unpleasant sound, a vibration, a pressure differential, an electrical shock, a high frequency, or a flash of light.

A further understanding of the nature and advantages of the present invention may be realized by reference to the remaining portions of the specification and the drawings.

DESCRIPTION OF THE SPECIFIC EMBODIMENTS

The present invention includes at least one technique for monitoring an undesired behavioral disorder such as bruxism, jaw clenching, or snoring. A processor correlates the monitored behavior with the onset of the undesired disorder. Since behavior of this type is typically subconscious, the sensor is coupled to a warning device to alert the patient when he or she is performing the undesired behavior. One type of warning device causes the patient to experience an unpleasant sensation, thus promoting the discontinuance of the behavior. In one embodiment of the invention, if the control system senses that the behavior continues after activation of the warning device, the output of the warning device may be increased, varied, or combined with some other output. Thus in this configuration the system determines which stimuli is most effective and therefore best suited for an individual patient.

The invention may further include an intervention means which can apply stimulation directly to the jaw muscles to force the jaws to open. The intervention device can also overstimulate and thus temporarily paralyze the jaw muscles, thereby preventing the muscles from contracting.

Additionally, the present invention may include means to record the monitored data related to the undesired behavioral disorders. This feature allows the patient to receive data related to the rate, duration, and time of day that the unconscious behavior occurred thus enabling the patient to avoid circumstances that tend to cause the undesired behavior (e.g., stress, lack of sleep, etc.).

Figure 1:
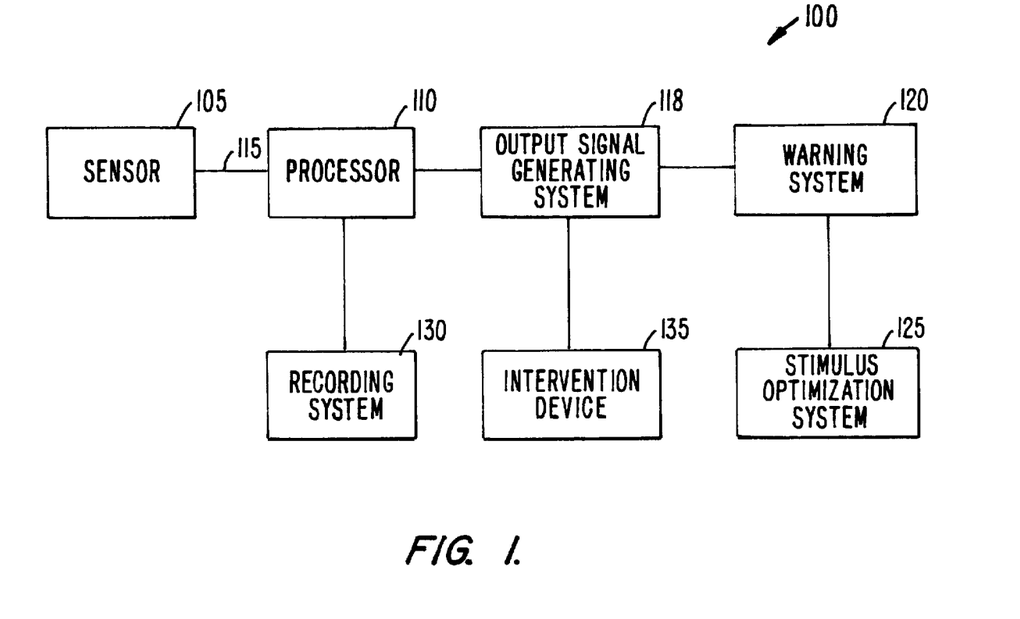
FIG. 1 is a schematic illustration of the principal elements of the invention.

FIG. 1 is a schematic representation of one embodiment of the invention. System 100 generally includes a sensor 105 and a processor 110. Sensor 105 detects changes in the patient that are associated with the undesired behavior. For example, the patient may emit a sound during the behavior (e.g., snoring, teeth grinding, etc.) or contract a muscle (e.g., jaw clenching, teeth grinding, etc.). Typically sensor 105 and processor 110 are hardwired together and are preferably contained within a single housing. However, processor 110 may be remote from sensor 105 and coupled through a communication link 115. Communication link 115 may be a wire cable, a RF communication link, an infrared communication link, or some other link well known by those of skill in the art. Allowing processor 110 to be positioned remotely from sensor 105 provides several benefits to the user. For example, this configuration allows the miniaturization of sensor 105 to be optimized, resulting in a less obtrusive sensor.

In one embodiment of system 100, processor 110 determines the rate at which the undesired behavior occurs (i.e., the number of occurrences per time interval) and the relative intensity of each occurrence (e.g., a very loud snore compared to a relatively quiet snore). In at least one embodiment of the invention, processor 110 also determines the duration of each occurrence. In some instances durational information is very important. For example, the system may indicate that a person only snores for a short period of time before self correcting (e.g., snores for 2 minutes and then automatically changes sleeping position to prevent the continuance of the snoring).

Besides determining characteristics of the undesired behavior such as rate, duration, and intensity, processor 110 also preferably compares at least one such characteristic to a pre-selected value. For example, assuming that the pre-selected value is a rate, processor 110 determines whether or not the rate at which the undesired behavior is occurring exceeds the pre-selected rate prior to taking further action. Once processor 110 determines that the triggering criterion has been met, processor 110 causes circuitry 118 to output an appropriate signal. The output signal may be a simple binary signal representing the occurrence of an event, or a more complex signal representing not only the occurrence of an event, but also the intensity associated with the event.

The use of a pre-selected value offers several benefits. First, it prevents system 100 from triggering a response to a non-event. For example, in one embodiment the pre-selected value is an intensity level and sensor 105 monitors sound. By setting the pre-selected value to a sufficiently high value, only the sounds associated with 'loud' snoring will trigger the system, not standard breathing sounds. Second, by comparing a characteristic of an event to a pre-selected value, the system can be designed to allow the patient to naturally cure the problem as opposed to being overly reliant on system 100. For example, although a person may be prone to snoring, they may naturally quit snoring within a relatively short period of time. Third, in at least one embodiment of the invention the pre-selected value may be changed, thus allowing the triggering value to change as the patient's behavior improves. For example, initially it may be desirable to trigger the system for every occurrence of teeth grinding. Later, after the patient has undergone behavioral modification therapy for a while, it may be desirable to allow the patient to grind their teeth for a short period of time, thus providing the patient time to subconsciously recognize and cease the undesired behavior.

In yet another aspect of the invention, processor 110 is coupled to a warning device 120 through output generating circuitry 118. Thus warning device 120 is activated by the output of a signal through circuitry 118. Typically warning device 120 is coupled directly to circuitry 118, preferably through a direct hardwired coupling. Alternatively, warning device 120 may be indirectly coupled to circuitry 118 through, for example, a non-obtrusive infrared, RF, or other link. Whether the link to warning device 120 is hardwired or non-obtrusive is primarily driven by the type of warning alert system in use. For example, if warning device 120 is a vibratory device contained within a belt, the belt designed to encircle some portion of the body (e.g., wrist, ankle, waist, neck, etc.), a non-obtrusive link is best since this allows the patient unrestrained movement. If, on the other hand, sensor 105 is designed to fit within the ear channel of the user and warning device 120 is designed to emit an audible tone, warning device 120 is preferably hardwired and contained within the same enclosure that houses the other system components.

In a preferred embodiment, warning device 120 is an aversion therapy device whereby the patient is discouraged from the involuntary and subconscious behavioral disorder (i.e., clenching, grinding, or snoring). Typically the aversion device not only reminds the patient that the undesired behavior is occurring, but also helps condition the patient against continuing such behavior. In order to accomplish these goals, device 120 preferably emits one or more stimuli that the patient finds generally annoying and unpleasant. The patient gradually and subconsciously learns the relationship between the undesired behavior and the unpleasant stimuli, thus learning to avoid the behavior in order to avoid the stimuli.

In another embodiment of the invention, warning device 120 is coupled to a stimulus optimization system 125. Typically system 125 is comprised of a logic sensor. System 125 is used to determine what stimulus is most effective for a specific individual, thus providing optimal aversion therapy. For example, assuming warning device 120 emits an audible tone, it is possible that while the emitted tone is extremely annoying to one person, a second person may find the tone indistinguishable over the background noise. Thus the tone would only be useful as an aversion therapy device for one of the people. In this example system 125 would be used to control the tonal frequency, the tonal intensity, or both. Therefore system 125 would determine the suitable aversion therapy tone for each patient, insuring that both users receive an appropriate alert tone.

In use, system 125 determines the appropriate stimuli in response to the data from processor 110. Processor data may include, for example, rate, duration, intensity, and time of day for each occurrence of the undesired disorder. By correlating this data with the output from device 120, system 125 determines whether or not the patient is responding appropriately to the aversion warning therapy. For example, a sleeping patient may be subjected to a vibration on the skin while sleeping during a clenching episode. If system 125 determines that the patient has not released the antagonistic jaw muscles in response to an initial stimuli, aversion therapy warning device 120 may be made, for example, to either increase the vibration amplitude or sound an audible alarm to wake the patient. Preferably data relating to the success of a particular stimuli is stored in memory thus allowing the system to apply the aversion therapy most suited for a patient based on historical data.

In yet another aspect of the invention, system 100 further comprises a recording system 130. Recording system 130 receives data from processor 110 and stores that data for access by the patient and/or the patient's doctor. Preferably recording system 130 records data relating to the duration, rate, intensity, and time of day for each episode of the undesired behavior. Additionally, data may be recorded relating to the output of warning device 120. For example, if an audible warning is sounded by device 120, recording system 130 will note the output of device 120 (e.g., intensity of warning output, duration, etc.) as well as the length of time that it takes the patient to respond. Since typically the behavioral disorder is performed unconsciously, and often while the patient is asleep, recording system 130 allows the patient to correlate the times and dates during which the behavior occurred with other life events. For example, if a patient's teeth grinding episodes only occur during or immediately after the performance of an unpleasant task at work or interaction with a specific person, it is probably safe to assume that there is a direct correlation between the life event and the behavioral disorder.

In order to minimize any inconvenience to the patient and avoid dramatically affecting the patient's activities, recording system 130 is preferably positioned remotely from the patient. Although the communication link between processor 110 and recording system 130 may be hardwired, preferably a non-obtrusive communication link is used such as provided by either a RF or infrared communication means.

In another aspect of the invention, the output from system 118 is used to activate an intervention device 135, either alone or in combination with warning device 120. For example, if the disorder in question is jaw clenching, intervention device 135 provides a means for applying direct stimulation to the antagonistic jaw muscle group (e.g., temporalis or masseter muscles). The stimulus is applied in such a manner as to cause the patient to subconsciously relax the antagonistic muscles. In extreme cases, the stimulus may include an electric pulse or shock. This form of stimulus will be of a degree sufficient to over-stimulate the jaw muscle group thereby temporarily paralyzing the muscle.

As briefly indicated in reference to FIG. 1, the present invention may utilize a variety of different sensors 105 and warning systems 120. Futhermore, system 100 may or may not include recording system 130 and intervention device 135. Additionally, if recording system 130 is used, warning system 120 may or may not be used. Primarily the circumstances surrounding the disorder mandate the type of system used, although other factors such as cost, size, therapy goals, and personal preferences will also impact system 100.

Provided below are a number of different designs for sensor 105 as well as warning system 120. As noted above, these various designs may be combined in a variety of ways in order to suit the needs of the user. Additionally, the manner in which they are linked together may vary from hardwiring to infrared and RF invisible links.

Sensors

In one embodiment of the invention, sensor 105 is used to monitor changes in a group of muscles. Typically the muscles under observation are jaw muscles although other muscles may be used, such as those found in the temple region or neck region. It is well known that muscle properties vary relative to the degree of contraction that a muscle experiences. The muscle properties that are most helpful in this respect are muscle thickness, muscle hardness, muscle resiliency, muscle electrical conductivity, muscle physical dimension, and muscle elasticity. Monitoring the flexure or contraction of these muscles provides an indicator of such undesired behavior as jaw clenching and teeth grinding.

Muscle flexure or contraction may be monitored either directly or indirectly. For example, as the patient undergoes a period of jaw clenching, various muscles contract, including the muscles in both the jaw and the temple. By placing any of a variety of sensors described more fully below proximate to the jaw or the temple, the occurrence of jaw clenching may be directly monitored. Alternately, this occurrence may be monitored indirectly by observing the effects of the muscle contraction on a different area of the patient. This capability is a result of the tissue distortion caused by the muscle contraction. For example, as the jaw muscles contract, the size and shape of the ear channel is distorted. Therefore by placing a transducer (e.g., force transducer, piezoelectric transducer, displacement transducer, etc.) within the ear channel, jaw muscle flexure resulting from such behavior as teeth grinding and jaw clenching may be indirectly monitored and used by the system to determine the occurrence of undesirable behavior.

Figure 2:
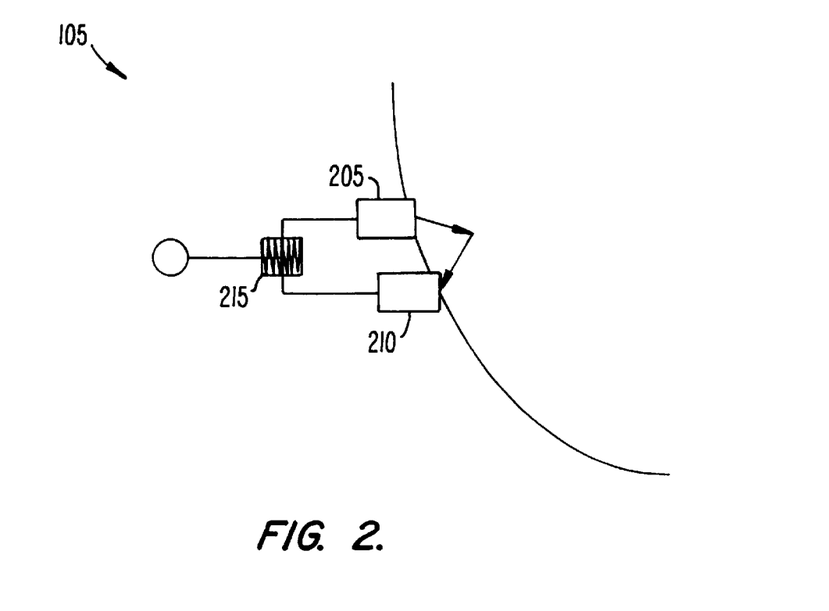
FIG. 2 is an illustration of a sensor for sensing changes in muscle properties.

FIG. 2 is an illustration of a sensor 105 for sensing changes in muscle properties. In this embodiment sensor 105 is comprised of an emitter 205 and a receiver 210 that may or may not be combined into a single transceiver. Emitter 205 emits a wave of a predefined frequency, for example, a vibrational wave, a sound wave, or an ultrasonic wave. Receiver 210 receives the reflected wave. In one configuration, circuitry 215 determines the amount of time that it takes a wave to be reflected by the muscles in question. Alternatively, the attenuation of the intensity of the reflected waves may be monitored. As the properties of the muscles change (e.g., muscle flexure), both the wave reflection time and the attenuation factor change. Therefore in this embodiment processor 110 determines whether or not a behavioral disorder is occurring based on the wave reflection time or, alternatively, reflected wave intensity.

Figure 3:
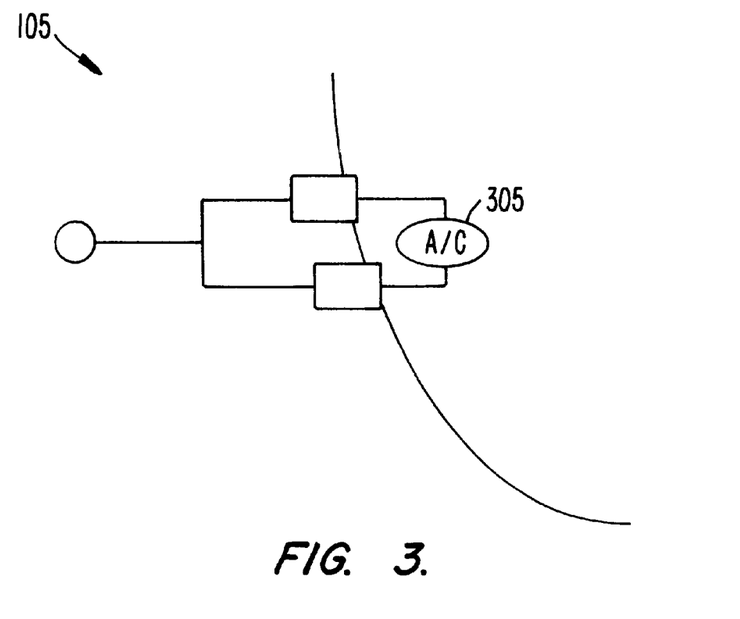
FIG. 3 is an illustration of a muscle flexure sensor utilizing changes in the electrical conductivity of the muscle tissue.

In an alternative muscle flexure sensor illustrated in FIG. 3, variations in the electrical conductivity and/or electrical activity of the muscle tissue are monitored as the muscle contracts. In one configuration the variation in the electrical conductivity of the jaw muscles is measured by passing a current, preferably an alternating current, through a patient's skin by means of a capacitive coupler 305 or similar device. Alternatively, coupler 305 may simply measure the electrical signals, typically on the microvolt level, that are emitted by the muscles as they contract.

Figure 4:
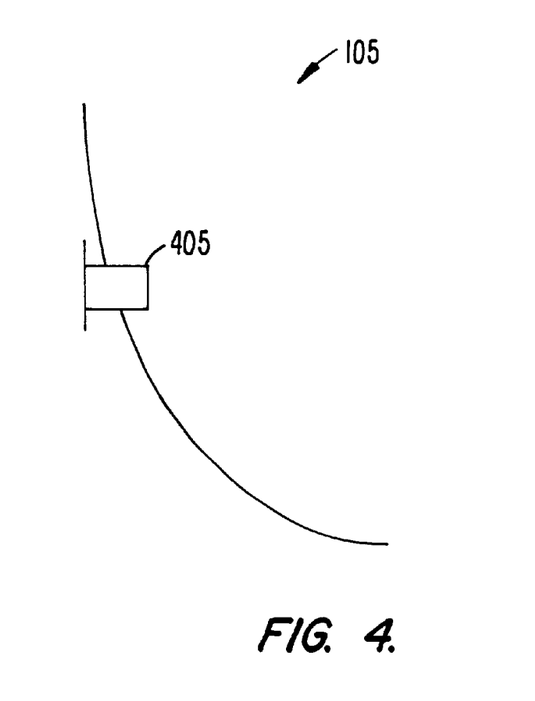
FIG. 4 is an illustration of a muscle flexure sensor utilizing changes in the physical dimensions of the muscle.

FIG. 4 is an illustration of another embodiment of muscle flexure sensor 105. In this embodiment sensor 105 monitors variations in the physical dimensions of the muscles, through the use of a pressure, force, motion, strain, or displacement transducer 405. Although such transducers are well known by those of skill in the art, examples of suitable detectors include piezoelectric thin films, magnetic dynamic pick-ups, and strain gauges. The transducers may be easily applied to the area of interest, for example, through the use of an adhesive tape. Suitable areas include portions of the neck, face (e.g., temple), jaw, and ear channel. In use, when the muscle in question contracts, it tends to form a small, compacted mass of muscle tissue. When this occurs, sensor 405 monitors the change. For example, the amount of displacement monitored by a displacement transducer indicates the relative amount of muscle contraction.

Figure 5:
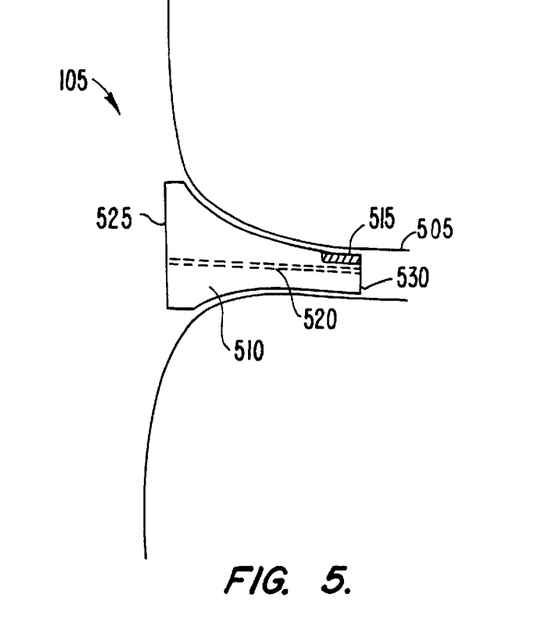
FIG. 5 is an illustration of a sound monitoring sensor for use in the ear channel.

In another embodiment of the invention illustrated in FIG. 5, sensor 105 monitors sound. The sound may be due to snoring or teeth grinding. Since often times jaw clenching is associated with at least some amount of teeth grinding, the sensor may be used to modify this behavior as well. In this embodiment sensor 105 fits within an ear channel 505 of the patient. Sensor 105 is comprised of an ear plug 510 and a microphone 515.

In one configuration, plug 510 is fabricated of a porous material thus allowing the patient to continue to hear external sounds. In a second configuration, plug 510 is fabricated of a solid material and includes a hollow tube 520 extending from an exterior plug surface 525 to an interior plug surface 530. Allowing the patient to hear external sounds is beneficial for several reasons. First, it insures that the patient is able to hear noises that are associated with emergency services, for example fire alarms, burglar alarms, etc. Second, it allows the patient to use system 100 even while awake, thus helping to modify subconscious behavior such as teeth grinding that may occur even during waking hours.

Figure 6:
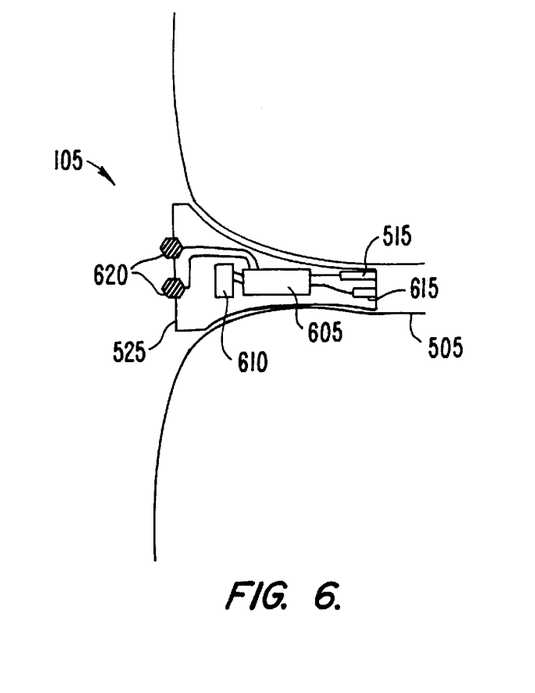
FIG. 6 is an illustration of a completely self contained system designed to fit within a single ear plug.

FIG. 6 is an illustration of system 100 that is completely contained within a single plug 510 although various alternate configurations may be used depending upon the system design goals. The output of microphone 515 is directly coupled to a processor 605. Processor 605 is powered by a battery 610, similar to that used in common hearing aids. When the sound detected by microphone 515 is sufficiently loud, indicating the occurrence of an undesirable behavioral pattern (e.g., snoring, teeth grinding, etc.), processor 605 outputs a signal to a miniature speaker 615. Speaker 615 then emits an audible tone or, in one configuration, a digitally recorded voice message, that is used to modify the patient's behavior. In a preferred embodiment, plug 510 includes one or more switches 620 that are mounted to external surface 525 of the plug. Switches 620 are coupled to processor 605 and may be configured to control such system functions as power on/off, the sound level necessary to trigger a system output, the volume of the warning emitted by device 615, and the frequency of the warning emitted by device 615.

Figure 7:
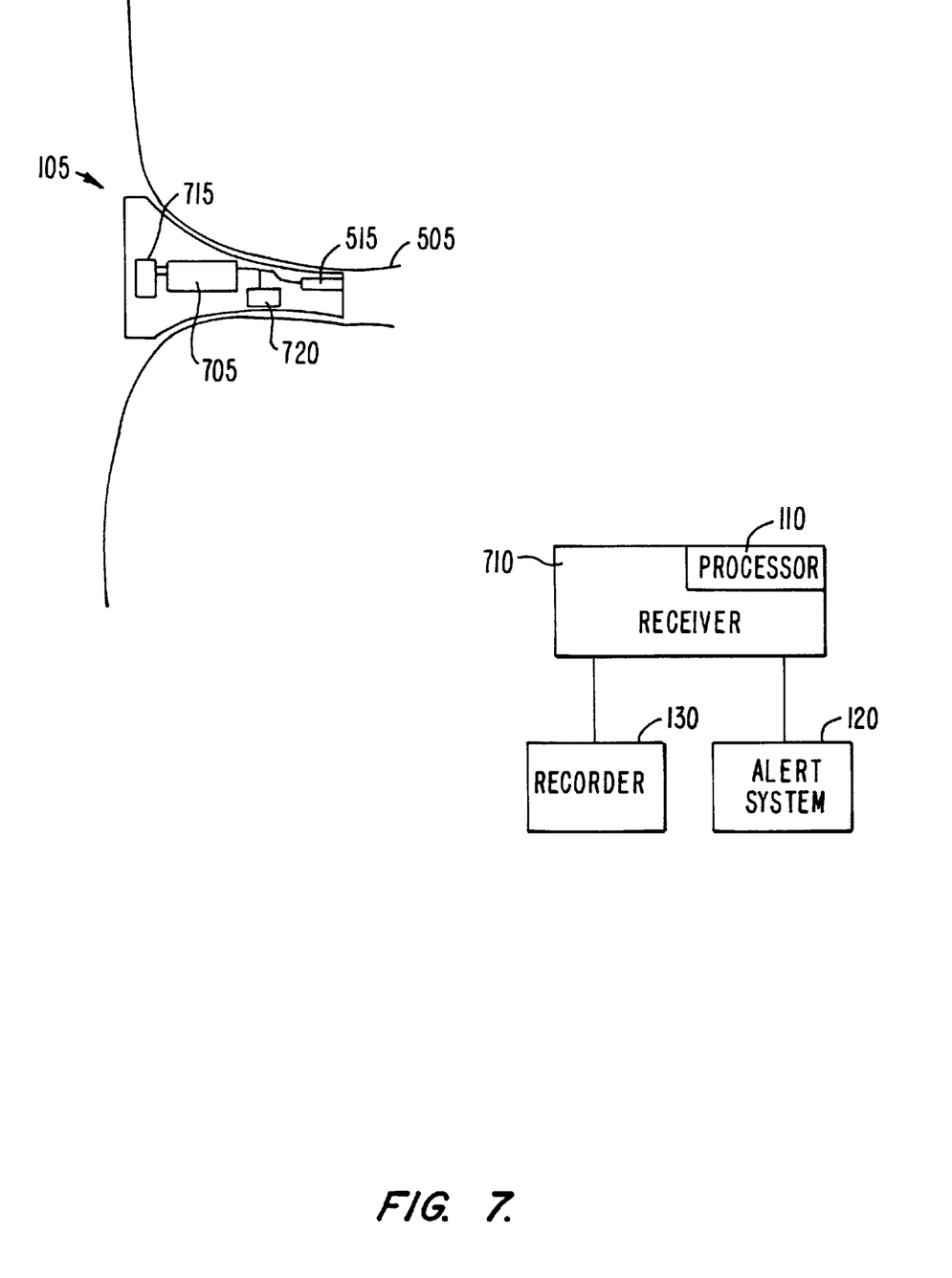
FIG. 7 is an illustration of a sound monitoring sensor mounted within an ear plug that is used to transmit data to a remotely located processing system.

In the embodiment of sensor 105 shown in FIG. 7, the output from microphone 515 is transmitted via a transmitter 705 to an external receiver 710. Receiver 710 includes processor 110 and is used to control such external devices as recorder 130, warning system 120, or both. Transmitter 705 is powered by a miniature battery 715. Alternatively, the signal from microphone 515 may be pre-processed by a processor 720 prior to being transmitted by transmitter 705 to receiver 710.

Figure 8:
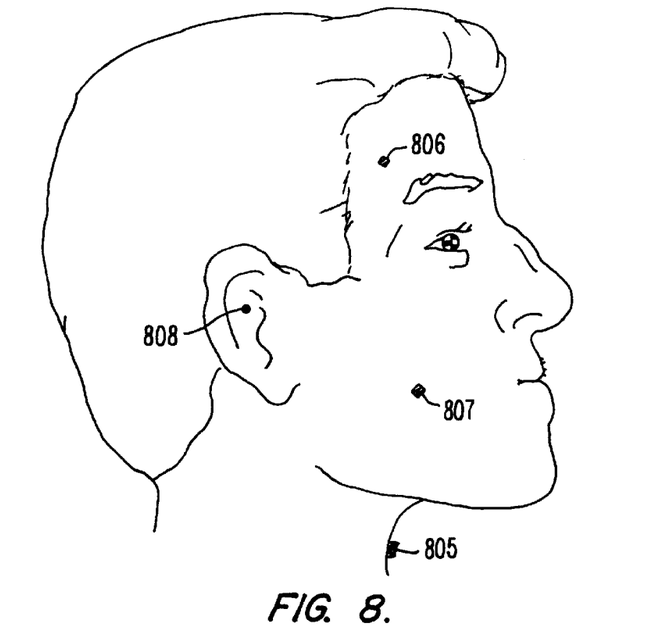
FIG. 8 is an illustration of a system designed to monitor sound that is conducted through the user's tissue.

In another embodiment of the invention illustrated in FIG. 8, sensor 105 monitors sound emitted by the patient during each occurrence of the undesired behavior. In this embodiment the sound is not received as audible sound waves passing through the air. Rather, in this embodiment the sound is conducted through the user's tissue to one or more sound pick-ups 805–808. Sound conduction through tissue (e.g., bone tissue, muscle tissue, fat tissue, sinew tissue) is a well known phenomena. In this embodiment the sound emitted by such disorders such as snoring and teeth grinding is conducted through the user's tissues until it reaches a system pick-up. The system pick-up may be located on the neck (i.e., pick-up 805), on a portion of the face such as the temple (i.e., pick-up 806), the jaw (i.e., pick-up 807), or within the ear channel (i.e., pick-up 808). The output from the pick-up may either be transmitted directly to a remote receiver or processed and then transmitted to the remote receiver. The transmission may either be through wire or using a wireless system as described above (i.e., a RF or infrared system).

Figure 9:
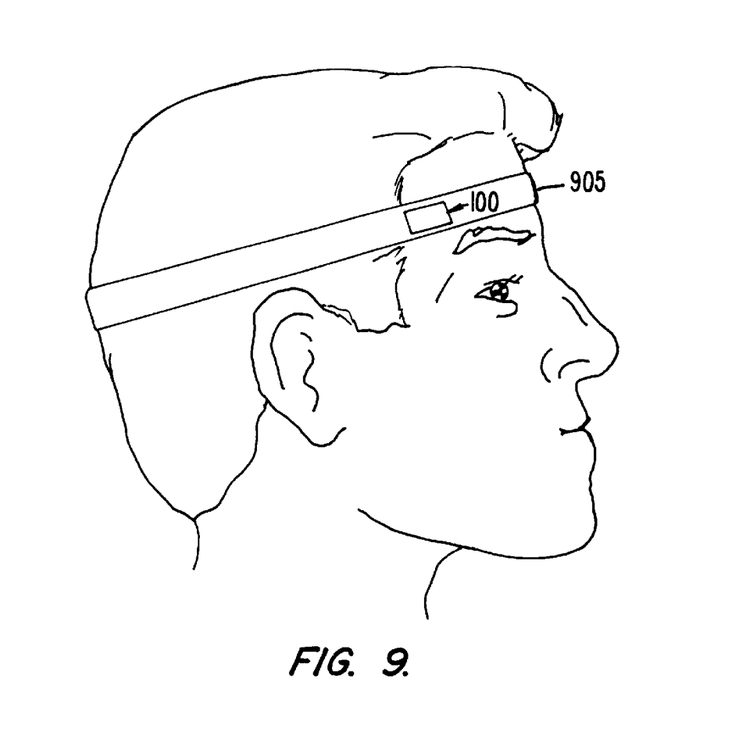
FIG. 9 is an illustration of a head band system used to maintain the sensor in place.
Figure 10:
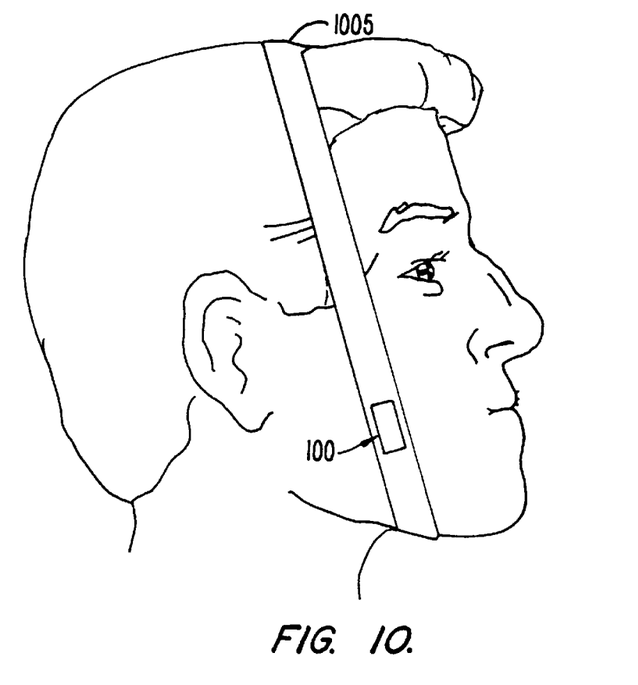
FIG. 10 is an illustration of an alternate embodiment of a sensor locating elastic band.
Figure 11:
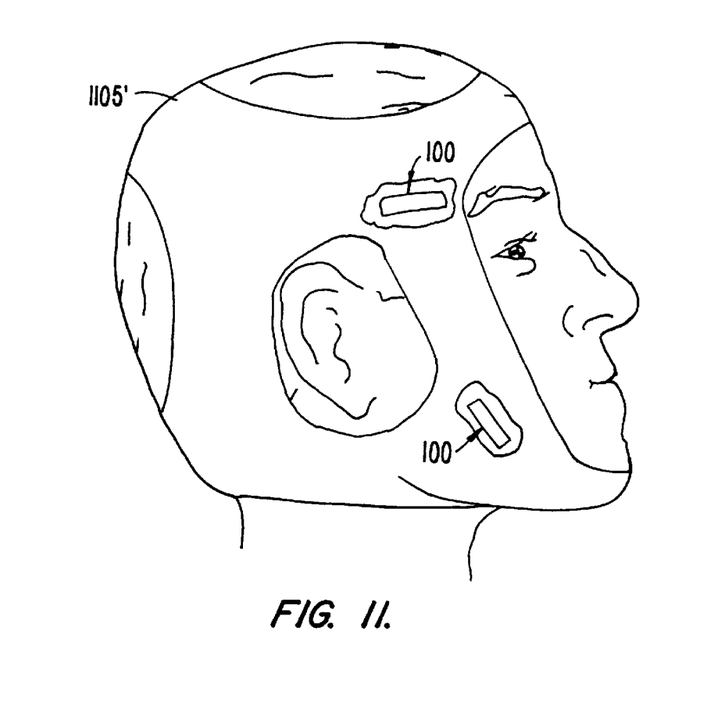
FIG. 11 is an illustration of a sensor locating system utilizing an elastic skull cap.

Sensor 105, depending upon the type of sensor, is mounted to the user in one of several manners. For example, the ear plug system illustrated in FIGS. 5–7 undergoes slight compression during insertion into the user's ear channel. Once the plug is in place it expands slightly, thereby keeping it in place. Sensors 105 that are mounted to an external surface of the user may utilize a light adhesive on the mounting surface, the adhesive holding the sensor to the user. Alternatively, the sensor may be held in place with an adhesive tape. Alternatively, the sensor may be held in place with an elastic band. As illustrated in FIG. 9, an elastic head band 905 wraps around the patient's head from back to front. System 100 is strategically located over the temporal body region such that sensor 105 is located proximate to the temporalis muscle. In FIG. 10, an elastic band 1005 is used which wraps around the patient's head from the top of the skull to around the lower jaw. In this example system 100 and sensor 105 are strategically located proximate the masseter muscle. The systems illustrated in FIGS. 9 and 10 may comprise more than one sensor and may be used in tandem with each other. FIG. 11 illustrates an alternate configuration utilizing a skull cap 1105. Cap 1105 is worn over the entire head, with face, ears, and portions of the head exposed for comfort. System 100 is placed proximate the desired sensing locations, for example the masseter and temporalis muscle locations as shown. Due to the large surface area of cap 1105, multiple sensors, processors, alert systems, etc. may be used in a simultaneous fashion. The cap is preferably made of an elastic, stretchable material such as spandex.

In alternative embodiments of the invention, a detector is mounted between the patient's teeth. The detector preferably comprises a bite guard or a pressure plate which is used to sense the force created by the act of the patient clenching or bruxing his or her teeth. The detector provides information to a dentist which will include information on pressure points created when a patient's upper teeth engage with the patient's lower teeth. In another alternative, the detector includes an environmental pressure sensor that is located in the patient's mouth for detecting a pressure change within the mouth when the patient clenches his or her teeth. For example, the pressure within a patient's mouth tends to increase when the lips are tightly closed. When the teeth are then clenched together, the mouth becomes a closed cavity and variations in environmental pressure can be sensed. In yet another alternative, the detector includes electronic circuitry physically attached to the upper or lower teeth to sense the proximity of the lower and upper teeth. In this alternative, the circuitry includes a means for determining the length of time that the teeth are in contact with each other to prevent nuisance warnings when the patient simply opens and closes his or her mouth. In yet another alternative, the invention includes an occlusion pressure sensitive element comprising a number of pressure sensitive layers that change electrical characteristics when subjected to external pressure. Typically, the pressure sensor will comprise a number of strip electrodes on either side of a pressure sensitive layer to electrically couple the pressure sensitive layer to another device.

Warning Systems

The stimulus from warning device 120 may take any form that causes the patient to alter their behavior. For example, device: 120 may produce; (i) an odor, (ii) a change in temperature, either hot or cold, preferably to a localized region of the patient (e.g., from a heat lamp or electrical heater), (iii) an unpleasant sound (e.g., loud or tonally unpleasant sounds), (iv) vibration applied to a portion of the skin or mucus membrane, (v) vibration applied to the individual through indirect coupling to a vibratory pad or other vibratory mechanism, (vi) an application of pressure, preferably by a sharp object, (vii) an application of pressure inside the mouth (e.g., to the soft pallet) or outside the mouth (e.g., below the chin), (viii) an electrical shock, (ix) an application of a high frequency, or (x) a flash of light.

In at least one embodiment of the invention, warning device 120 is a sound unit that emits an audible tone. Preferably the sound is emitted through a speaker which may be located proximate to, or within, the patient's ear. Alternatively, the speaker may be located on the patient's body in such a manner as to cause the sound to be conducted through the patient's tissue (i.e., bone, muscle, fat, and sinew tissue) so that the patient still "hears" the warning sound. Alternatively, the sound unit can be positioned remotely from the patient, for example, on a nightstand located next to the bed. Preferably warning device 120 further comprises a cut-off mechanism that shuts-off the audible tone or other signal after a reasonable time has passed. Alternatively, device 120 may be designed to automatically shut-off after the cessation of the undesirable behavior.

In an alternative embodiment, warning device 120 generates vibrations. Preferably in this embodiment device 120 is directly coupled to the patient. For example, device 120 may be mounted within an elastic band to be worn by the patient around some body portion (e.g., wrist, ankle, neck, waist, etc.). Alternately, device 120 may be mounted within a bed pad on which the patient lies.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A behavioral modification device for modifying undesired behavioral patterns, wherein said undesired behavioral patterns are selected from the group consisting of bruxism, jaw clenching, and snoring, said device comprising;

a monitor, wherein at least a portion of said monitor is adapted to fit within an ear channel of a user, said monitor detecting an indicator of a muscle flexure associated with said undesired behavioral pattern, said monitor including at least one muscle contraction measuring device for monitoring distortion of said ear channel due to said muscle flexure associated with said undesired behavioral pattern;

a discriminator for comparing said indicator with a predetermined criteria, wherein said discriminator outputs a signal when said indicator matches said predetermined criteria; and     an alert system for alerting said user of an occurrence of said undesired behavioral pattern, wherein said alert system responds to said output signal.

2. The behavioral modification device of claim 1, wherein said alert system is selected from the group consisting of light controllers, temperature regulators, odor generators, high frequency generators, tactile pressure generators, vibratory generators, sound generators, and electric shock generators.

3. The behavioral modification device of claim 2, wherein said vibratory generator is coupled to said user with a flexible belt coupler designed to encircle a portion of said user.

4. The behavioral modification device of claim 2, wherein said vibratory generator is coupled to a bed pad.

5. The behavioral modification device of claim 2, wherein said sound generator is coupled to said monitor, wherein an alert sound generated by said sound generator is generated within said user ear channel.

6. The behavioral modification device of claim 2, wherein said sound generator is coupled to said monitor, wherein an alert sound generated by said sound generator passes through said user ear channel to be preferentially heard by said user.

7. The behavioral modification device of claim 1, further comprising a transmitter coupled to said monitor for transmitting an output indicator signal representative of said indicator to a receiver coupled to said discriminator.

8. The behavioral modification device of claim 1, further comprising a transmitter coupled to said discriminator for transmitting said signal when said indicator matches said predetermined criteria and a receiver coupled to said alert system for receiving said signal.

9. The behavioral modification device of claim 1, wherein said predetermined criteria are comprised of a threshold intensity value and a rate criteria, wherein said discriminator only outputs said signal when an intensity level associated with said indicator exceeds said threshold intensity value at a rate greater than said rate criteria.

10. The behavioral modification device of claim 1, wherein said predetermined criteria is a threshold intensity value, wherein said discriminator only outputs said signal when an intensity level associated with said indicator is greater than said threshold intensity value.

11. The behavioral modification device of claim 1, wherein said at least one muscle contraction measuring device is a displacement transducer.

12. The behavioral modification device of claim 1, wherein said at least one muscle contraction measuring device is a pressure transducer.

13. The behavioral modification device of claim 1, further comprising a recording system, said recording system storing a record of said output signals.

14. A behavioral modification device for modifying undesired behavioral patterns wherein said undesired behavioral patterns are selected from the group consisting of bruxism and jaw clenching, said device comprising:

a transducer coupled to a facial segment of a user, said transducer detecting a change in muscle contraction in a muscle associated with said facial segment, wherein said transducer is selected from the group consisting of pressure transducers, force transducers, and piezoelectric transducers;

a discriminator for comparing said muscle contraction change with a threshold value, wherein said discriminator outputs a signal when said muscle contraction change exceeds said threshold value; and an alert system for alerting said user of an occurrence of said bruxism, wherein said alert system responds to said output signal, wherein said alert system is selected from the group consisting of light controllers, temperature regulators, odor generators, high frequency generators, tactile pressure generators, vibratory generators, sound generators, and electric current generators, wherein a charge from said electric current generators causes relaxation of at least one jaw muscle.

15. The behavioral device of claim 14, wherein said facial portion is a temple.

16. A behavioral modification device for modifying undesired behavioral patterns, wherein said undesired behavioral patterns are selected from the group consisting of bruxism and jaw clenching, said device comprising:

a transducer proximate to a jaw muscle of a user, said transducer detecting jaw muscle contraction, wherein said transducer is selected from the group consisting of pressure transducers, force transducers, and piezoelectric transducers;

a discriminator for comparing said jaw muscle contraction with a threshold value, wherein said discriminator outputs a signal when said jaw muscle contraction exceeds said threshold value; and an alert system for alerting said user of an occurrence of said bruxism, wherein said alert system responds to said output signal, wherein said alert system is selected from the group consisting of light controllers, temperature regulators, odor generators, high frequency generators, tactile pressure generators, sound generators, and electric current generators.

17. A behavioral modification device for modifying undesired behavioral patterns are selected from the group consisting of bruxism, jaw clenching, and snoring, said device comprising:

a monitor coup led to a facial portion or a neck portion of a user, said monitor measuring an indicator of muscle contraction in said facial portion or said neck portion, said muscle contraction indicative of said undesired behavioral pattern, said monitor further comprising a displacement transducer;

a discriminator for comparing said indicator with a predetermined criteria, wherein said discriminator outputs a signal when said indicator matches said predetermined criteria; and a recording system for storing a record of said output signals.

18. A behavioral modification device for modifying undesired behavioral patterns are selected from the group consisting of bruxism, jaw clenching, and snoring, said device comprising:

a monitor coupled to a facial portion or a neck portion of a user, said monitor measuring an indicator of muscle contraction in said facial portion or said neck portion, said muscle contraction indicative of said undesired behavioral pattern, said monitor further comprising a pressure transducer;

a discriminator for comparing said indicator with a predetermined criteria, wherein said discriminator outputs a signal when said indicator matches said predetermined criteria; and a recording system for storing a record of said output signals.

\* \* \* \* \*